United States Patent
Sitler et al.

(10) Patent No.: US 12,087,400 B2
(45) Date of Patent: Sep. 10, 2024

(54) GENOMIC VARIANT RE-CLASSIFICATION

(71) Applicant: CERNER INNOVATION, INC., Kansas City, KS (US)

(72) Inventors: Brad Sitler, Crownsville, MD (US); Ayla Smith, Kansas City, KS (US); Marshall Summar, Kansas City, KS (US); Seth I. Berger, Kansas City, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 834 days.

(21) Appl. No.: 17/136,966

(22) Filed: Dec. 29, 2020

(65) Prior Publication Data
US 2022/0208302 A1 Jun. 30, 2022

(51) Int. Cl.
| | | |
|---|---|---|
| *G16B 20/20* | (2019.01) | |
| *G06F 16/2458* | (2019.01) | |
| *G06F 16/248* | (2019.01) | |
| *G06F 16/27* | (2019.01) | |
| *G06F 16/28* | (2019.01) | |
| *G06Q 10/0631* | (2023.01) | |
| *G16B 50/30* | (2019.01) | |
| *G16H 10/40* | (2018.01) | |
| *G16H 10/60* | (2018.01) | |
| *G16H 15/00* | (2018.01) | |
| *G16H 40/20* | (2018.01) | |
| *G16H 50/70* | (2018.01) | |
| *G16H 70/60* | (2018.01) | |

(52) U.S. Cl.
CPC ......... *G16B 20/20* (2019.02); *G06F 16/2465* (2019.01); *G06F 16/248* (2019.01); *G06F 16/27* (2019.01); *G06F 16/285* (2019.01); *G06Q 10/06312* (2013.01); *G16B 50/30* (2019.02); *G16H 10/40* (2018.01); *G16H 10/60* (2018.01); *G16H 15/00* (2018.01); *G16H 40/20* (2018.01); *G16H 50/70* (2018.01); *G16H 70/60* (2018.01)

(58) Field of Classification Search
CPC ..... G16B 20/20; G16B 50/30; G06F 16/2465; G06F 16/248; G06F 16/27; G06F 16/285; G06Q 10/06312; G16H 10/40; G16H 10/60; G16H 15/00; G16H 40/20; G16H 50/70; G16H 70/60
See application file for complete search history.

(56) References Cited

U.S. PATENT DOCUMENTS

| | | | | |
|---|---|---|---|---|
| 10,395,772 | B1 * | 8/2019 | Lucas | G16H 10/60 |
| 2020/0080132 | A1 * | 3/2020 | Madrid | C12Q 1/6883 |
| 2020/0176098 | A1 * | 6/2020 | Lucas | G16H 10/60 |
| 2020/0365268 | A1 * | 11/2020 | Michuda | G16H 50/20 |
| 2021/0090694 | A1 * | 3/2021 | Colley | G16H 15/00 |

OTHER PUBLICATIONS

Welch, Brandon Marshall. "Clinical Decision Support for the Whole Genome Sequence." Order No. 3620754 The University of Utah, 2014. Ann Arbor (Year: 2014).*

* cited by examiner

*Primary Examiner* — Amber A Misiaszek
(74) *Attorney, Agent, or Firm* — Kraguljac Law Group, LLC

(57) ABSTRACT

A computing platform is provided to perform continuous monitoring of new genomic variants from external genomic databases and compare the new variants to genomic sequencing results for patients stored in long term cloud storage. The platform provides alerts to clinicians if a patient's genomic sequencing results match one or more of the new genomic variants.

20 Claims, 4 Drawing Sheets

| CHROMOSOME | START | STOP | REFERENCE ALLELE | NEW ALLELE | STATUS |
|---|---|---|---|---|---|
| 11 | 108147395 | 108147395 | C | CC | BENIGN |
| 6 | 131873052 | 131873052 | T | TT | UNKNOWN |
| 6 | 152520544 | 152520544 | T | G | DISEASE A |
| 1 | 94078580 | 94078580 | C | G | UNKNOWN |
| X | 19358913 | 19358933 | TAGT... | TACT... | BENIGN |

*FIG. 4.*

GENOMIC VARIANT RE-CLASSIFICATION

BACKGROUND

Genetic testing and counseling for diagnosis and treatment is in its infancy. New genetic variants linked to rare diseases are discovered on a regular basis. As the field is evolving so rapidly, it is difficult in a diagnosis and treatment environment for clinicians to keep up with all of the new variants. As such, even when a patient has undergone genetic sequencing, clinicians often have an incomplete genetic picture for the patient and do not have a way to continuously monitor new developments in the genetic field.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present disclosure is defined by the claims as supported by the Specification, including the Detailed Description.

Embodiments of the present invention improve implementation and on-going costs of analyzing new genetic variants and discoveries as they apply to individual patients. Typically, patients with a genetic disease only receive a definitive genetic diagnosis 20 percent of the time after undergoing genomic sequencing. The remaining 80 percent will continue to follow up with the clinician, such as a genetic counselor, in the following years on a yearly or every other year basis. When a patient without a definitive genetic diagnosis follow ups with a clinician, the clinician manually reviews new genomic variants and discoveries that have occurred since the patient's first visit. Typically, this is done by the clinician or a laboratory group manually reviewing publicly and privately available databases having genetic variant information. The clinician then must manually compare the new variants to the patient's genomic sequencing performed years prior to that visit.

The manual process of reviewing and comparing new genomic variants against a patient's genomic sequencing from previous years is time consuming and error prone. A lot of data has to be reviewed and then manually compared by a clinician. Furthermore, new genomic variants and information are discovered on a weekly or monthly basis. Embodiments of the present invention address this problem by automatically comparing a patient's genomic sequencing results over time with new genetic variants and discoveries on a regular basis instead of just when the patient has a follow-up appointment with a clinician. This allows for faster genetic diagnosis of the patient. As new variants are discovered so are new treatments, such as medications, nutrition, monitoring and lifestyle changes. A patient may be able to obtain proper treatment years earlier than before using embodiments of the present invention.

Embodiments of the present invention decrease the manual labor/effort by a clinician or laboratory to track new genomic variants and compare to patient's genomic sequence. Utilizing embodiments of the present invention, once genomic sequencing results for patients are known to the platform, automated look-ups and queries are performed on a continuous basis as new genomic variants are discovered. This allows for earlier rare disease diagnosis for patients.

The platform decreases diagnosis costs and inappropriate treatment costs and complications. Earlier, more comprehensive clinical appointments are scheduled for undiagnosed rare diseases. Furthermore, it provides peace of mind for family and friends to know their child or loved one is being continually evaluated for new definitive diagnoses.

Whole genome sequencing provides the nucleotide sequence of an individual organism's, such as a human, DNA. Further analysis is performed to provide a biological or medical meaning of the sequence and how it can be used to treat a patient. Whole genome sequence generates a lot of data (six billion base pairs for each human genome). The data output is stored electronically and requires a large amount of computing power and storage capacity.

A system, method and computer readable-media useful in a cloud environment for determining a patient has a newly discovered genomic variant are provided herein. Genomic sequencing results for a patient are received and stored in a cloud database. An initiation request is received to access the genomic sequencing results for the patient from the cloud database. New genomic variants from a third-party database are accessed. Utilizing a computer processor, it is determined that the genomic sequencing results for the patient match the one or more of the new genomic variants. A graphical user interface presents an alert to a clinician of the match. A follow-up appointment with the clinician is scheduled for the patient to review the new genomic variant data. The genomic sequencing results for the patient are stored in inactive cloud storage. The initiation request to access the genomic sequencing results from inactive cloud storage is sent when pricing for computing power is below a pre-set threshold.

Embodiments of the present invention automatically load genomic variants for a patient with an undiagnosed genetic disease to a variant data store, in a healthcare cloud computing platform. In some embodiments, the variant data store is cold cloud computing storage that can be accessed when economically feasible.

BRIEF DESCRIPTION OF THE DRAWINGS

Illustrative aspects of the present invention are described in detail below with reference to the attached drawing figures, and wherein:

FIG. 4 depicts an exemplary database of new genetic variants in accordance with aspects of the invention.

DETAILED DESCRIPTION

The subject matter of the present invention is being described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Terms should not be interpreted as implying any particular order among or between various steps herein disclosed unless and except when the order of individual steps is explicitly described. As such, although the terms "step" and/or "block" can be used herein to connote different elements of system and/or methods, the terms should not be interpreted as implying any particular order and/or dependencies among or between various components and/or steps herein disclosed unless and except when the order of individual steps is explicitly described. The present disclosure will now be described more fully herein with reference to the accompanying drawings, which may not be drawn to scale and which are not to be construed as limiting. Indeed, the present invention can be embodied in many different forms and should not be construed as limited to the aspects set forth herein. Further, it will be apparent from this Detailed Description that the technological solutions disclosed herein are only a portion of those provided by the present invention. As such, the technological problems, solutions, advances, and improvements expressly referenced and explained herein should not be construed in a way that would limit the benefits, improvements, and/or practical application of the discussed aspects of the present invention.

Figure 1:
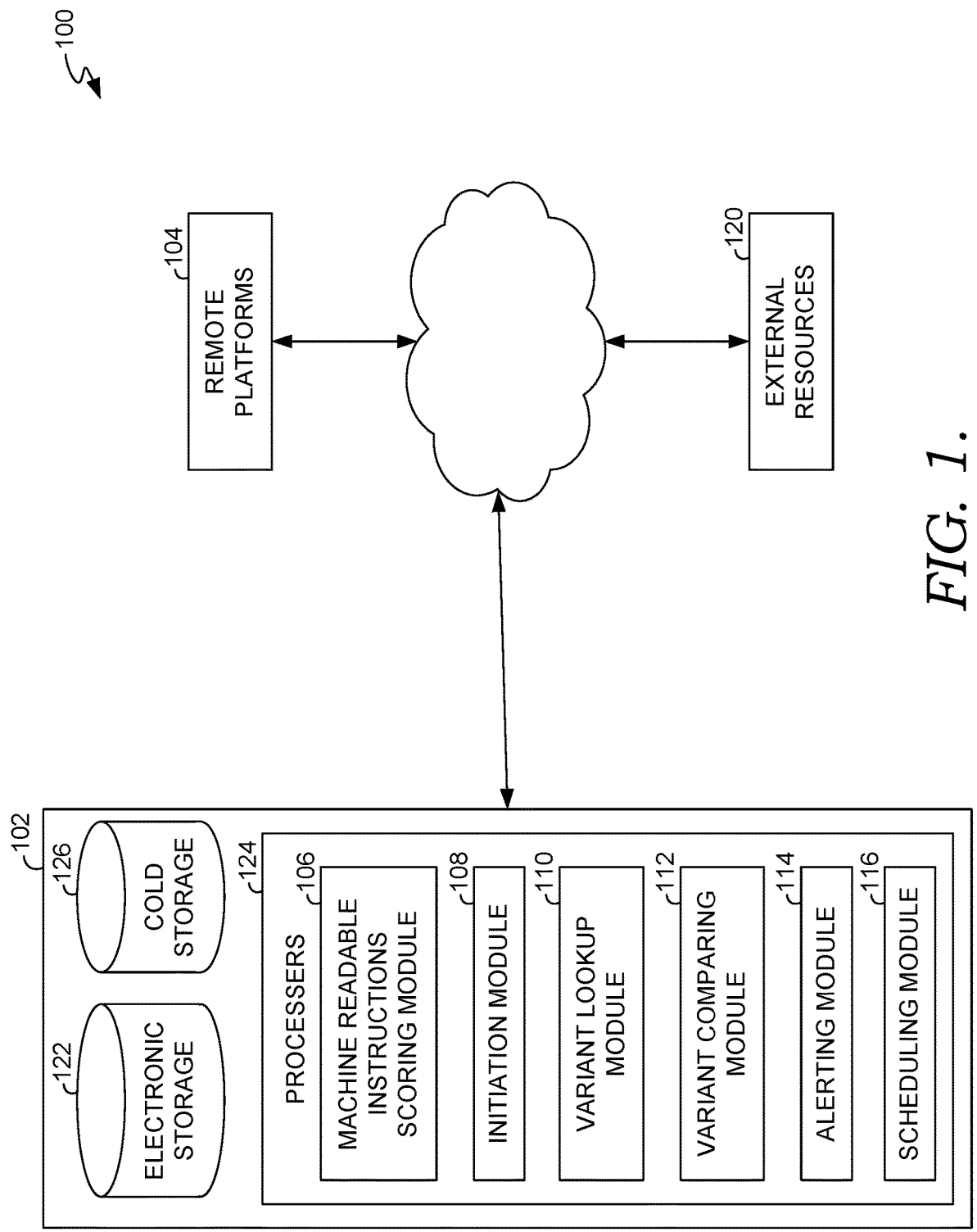
FIG. 1 illustrates a healthcare cloud computing platform, in accordance with aspects of the invention.

The healthcare cloud computing platform of embodiments of the invention advances notification of a clinician treating a patient of potential new genetic variants for a patient who has previously had whole genome sequencing. FIG. 1 illustrates a system 100 configured to be useful in a computer healthcare system to consume clinical quality language queries in a programmatic manner, in accordance with one or more implementations. In some implementations, system 100 may include one or more healthcare cloud computing platforms 102. Computing platform(s) 102 may be configured to communicate with one or more remote platforms 104 according to a client/server architecture, a peer-to-peer architecture, and/or other architectures. Remote platform(s) 104 may be configured to communicate with other remote platforms via computing platform(s) 102 and/or according to a client/server architecture, a peer-to-peer architecture, and/or other architectures. Users may access system 100 via remote platform(s) 104.

In some implementations, computing platform(s) 102, remote platform(s) 104, and/or external resource(s) 120 may be operatively linked via one or more electronic communication links. For example, such electronic communication links may be established, at least in part, via a network such as the Internet and/or other networks. It will be appreciated this is not intended to be limiting, and the scope of this disclosure includes implementations in which computing platform(s) 102, remote platform(s) 104, and/or external resource(s) 120 may be operatively linked via some other communication media.

A given remote platform 104 may include one or more processors configured to execute computer program modules. The computer program modules may be configured to enable an expert or user associated with the given remote platform 104 to interface with system 100 and/or external resource(s) 120, and/or provide other functionality attributed herein to remote platform(s) 104. By way of non-limiting example, a given remote platform 104 and/or a given computing platform 102 may include one or more of a server, a desktop computer, a laptop computer, a handheld computer, a tablet computing platform, a NetBook, a Smartphone, a gaming console, and/or other computing platforms.

External resource(s) 120 may include sources of information outside of system 100, external entities participating with system 100, and/or other resources.

Computing platform(s) 102 may include electronic storage 122, one or more processors 124, and/or other components. Computing platform(s) 102 may include communication lines, or ports to enable the exchange of information with a network and/or other computing platforms. Illustration of computing platform(s) 102 in FIG. 1 is not intended to be limiting. Computing platform(s) 102 may include a plurality of hardware, software, and/or firmware components operating together to provide the functionality attributed herein to computing platform(s) 102. For example, computing platform(s) 102 may be implemented by a cloud of computing platforms operating together as computing platform(s) 102.

Electronic storage 122 may comprise non-transitory storage media that electronically stores information. The electronic storage media of electronic storage 122 may include one or both of system storage that is provided integrally (i.e., substantially non-removable) with computing platform(s) 102 and/or removable storage that is removably connectable to computing platform(s) 102 via, for example, a port (e.g., a USB port, a firewire port, etc.) or a drive (e.g., a disk drive, etc.). Electronic storage 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 122 may include one or more virtual storage resources (e.g., cloud storage, a virtual private network, and/or other virtual storage resources). Electronic storage 122 may store software algorithms, information determined by processor(s) 124, information received from computing platform(s) 102, information received from remote platform(s) 104, and/or other information that enables computing platform(s) 102 to function as described herein. Cold storage 126 is cloud storage database for long-term storage of infrequently accessed data. Different methods of data retrieval are available at various speeds and costs from cold storage 126. Retrieval can take from a few minutes to several hours. Typically, cold storage 126 is different from electronic storage 122 as it is much less expensive in a cloud computing environment as data does not need to be accessed as frequently or quickly as data in electronic storage 122.

Processor(s) 124 may be configured to provide information processing capabilities in computing platform(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same device, or processor(s) 124 may represent processing functionality of a plurality of devices operating in coordination. Processor(s) 124 may be configured to execute modules 108, 110, 112, 114, and/or 116, and/or other modules. Processor(s) 124 may be configured to execute modules 108, 110, 112, 114, and/or 116, and/or other modules by software; hardware; firmware; some combination of software, hardware, and/or firmware; and/or other mechanisms for configuring processing capabilities on processor(s) 124. As used herein, the term "module" may refer to any component or set of components that perform the functionality attributed to the module. This may include one or more physical processors during execution of processor readable instructions, the processor readable instructions, circuitry, hardware, storage media, or any other components.

Platform 102 may be a cloud-based clinical electronic medical record (EMR) platform, such as Cerner HealthIntent® and/or Cerner Millennium®. External resource(s) 120 include third-party genetic or genomic databases, including, but not limited to, public repositories such as ClinGen™, GenBank®, Wiki Tree® and private genetic and genomic databases.

Cold storage 126 is a long-term database for patient genetic and genomic sequencing that resides in a cloud storage environment, such as AWS®. In one embodiment, a patient with an unknown disease and/or unknown genetic diagnosis visits a clinician, such as a genetic counselor or other specialist. The clinician places a medical order through platform 102 for the patient to have genomic testing performed. In another embodiment, a patient has genomic testing results that were previously performed. For example, in one embodiment, newborns or patients are screened for genetic markers or have complete genomic sequencing performed but do not have disease symptoms.

Genomic testing may include testing for suspected known genetic markers or may include sequencing the patient's entire genome. In one embodiment, the genomic testing may be single cell genomic sequencing. In one embodiment, the genomic testing includes mitochondrial DNA testing, chromosome studies, DNA studies, RNA studies and biochemical genetic studies.

In one embodiment, once the patient undergoes the ordered genomic testing, platform 102 receives the genomic testing results in response to the electronic medical order. The clinician reviews the results and known genetic variants and determines if the patient qualifies for one or more genetic diagnosis. The genomic test results for the patient are then placed into cold storage 126 for subsequent use by modules 108, 110, 112, 114 and/or 116 of platform 102. In another embodiment, genomic test results for a patient are transmitted to platform 102, the genomic test results for the patient are placed into cold storage 126 for subsequent use by modules 108, 110, 112, 114 and/or 116 of platform 102. The genomic test results for a patient are associated with their patient's electronic medical record and/or patient record number before being placed into cold storage 126. Cloud storage 126 maintains genomic sequencing results for patients.

It should be appreciated that although modules 108, 110, 112, 114, and/or 116 are illustrated in FIG. 1 as being implemented within a single processing unit, in implementations in which processor(s) 124 includes multiple processing units, one or more of modules 108, 110, 112, 114, and/or 116 may be implemented remotely from the other modules. The description of the functionality provided by the different modules 108, 110, 112, 114, and/or 116 described below is for illustrative purposes, and is not intended to be limiting, as any of modules 108, 110, 112, 114, and/or 116 may provide more or less functionality than is described. For example, one or more of modules 108, 110, 112, 114, and/or 116 may be eliminated, and some or all of its functionality may be provided by other ones of modules 108, 110, 112, 114, and/or 116. As another example, processor(s) 124 may be configured to execute one or more additional modules that may perform some or all of the functionality attributed below to one of modules 106, 108, 110, 112, and/or 114.

Computing platform(s) 102 may be configured by machine-readable instructions 106. Machine-readable instructions 106 may include one or more instruction modules. The instruction modules may include computer program modules. The instruction modules may include one or more of initiation module 108, variant lookup module 110, variant comparing module 112, alerting module 114, scheduling module 116, and/or other instruction modules.

Initiation module 108 receives an initiation request to access the genomic sequencing results for one or more patients from cold storage 126. Initiation module 108 may receive an initiation request when a patient schedules a new or follow-up appointment with a clinician. Initiation module 108 may be triggered based on bid spot pricing when the cost to use cloud computing resources drop below a certain threshold. For example, cloud computing resources may be less expensive from 2 a.m. to 4 a.m. on a Sunday morning. Platform 102 places bid spot purchasing of cloud computing resources and when the bid meets a threshold, initiation module 108 of platform 102 initiates cloud computing resources to access the genomic sequencing results for one or more patients. Utilizing bid spot processing to initiate cloud computing resources keeps the operating costs low such that variant lookup module 110 can be utilized more frequently when new variants are found in third-party genomic databases.

The bid for spot pricing will be initiated when the current market price for computer processing drops below a pre-set threshold. Once the cost for computer processing drops below the pre-set threshold, cloud computing resources are activated by initiation module 108 and variant lookup module 110 accesses and pulls genomic sequencing results from cold storage 126.

Variant comparing module 112 accesses new variants from external resource(s) 120. Variant comparing module 112 may do this on a regular basis and maintain a data store 122 of new variants from external resource (s) 120 to compare with genomic sequencing results for patients stored in cold storage 126 when initiated by initiation module 108. In another embodiment, variant comparing module 112 may query external resources when initiation module 108 initiates accessing genomic sequencing results for a patient.

In one embodiment, variant comparing module 112 extracts variants from a patient's genomic sequencing results in cold storage and compares the variants to new variants from external resources 120, such as national database(s), then records the results back to the cloud based data store of patients' variants.

Variant comparing module 112 runs a query against the new variants from external resources 120 and determines the status of the patient's current version of the new variant from the patient's genomic sequencing results. For example, with reference to FIG. 4, a data store of new variants from external resources is shown. For each new variant, the chromosome, start and stop points, reference allele, new allele, and status of the new allele are shown. It will be appreciated that any variety of data may be included in new variant data store and FIG. 4 is for illustrative purposes. In this example, for new variant 400, variant comparing module 112 determines the patient has the reference allele for the variant "C" for the new variant. In that instance, as the patient has the reference allele and there is no new information to report to the clinician, the platform 102 stores that the new variant 400 was queried against the patient's genomic sequencing results but did not yield new information. Thus, if the new variant comes up in future queries of new variants of external resources 120, platform 102 will know that the new variant has already been analyzed and does not need to use computing power to query the new variant against the patient's genomic sequencing results.

In this example, for new variant 400, variant comparing module 112 determines the patient has the reference allele for the variant "C" for the new variant. In that instance, as the patient has the reference allele and there is no change in patient's variant classification status and no new information to report to the clinician, the platform 102 stores that new variant 400 was queried against the patient's genomic sequencing results but did not yield new information. Thus, if the new variant comes up in future queries of new variants of external resources 120, platform 102 will know that the new variant has already been analyzed and does not need to use computing power to query the new variant subsequent times against the patient's genomic sequencing results. Typically, when the variant comparing module 112 does not find a change in classification status of a variant for the patient, alerting module 114 does not send an alert to a clinician as there is no new information for the clinician to review.

In this example, for new variant 405, variant comparing module 112 determines the patient has the new allele "TACT" for new variant 405 but that it is believed not to cause a known disease. As the patient has the new allele and there is change in patient's variant classification status the clinician is notified by alerting module 114 of the change. In another embodiment, the clinician is not alerted by alerting module 114 as the new allele is "benign" and it is unlikely to be associated with a disease. Platform 102 stores the new variant 405 and updates the variant classification for the patient. Platform 102 also stores that the new variant has been queried against the patient's genomic sequencing result, the changed classification and that the new variant is benign.

In this example, for new variant 415, variant comparing module 112 determines the patient has the new allele "TT" for new variant 415. As the patient has the new allele and there is change in patient's variant classification status the clinician is notified of the change by alerting module 114. In another embodiment, the clinician is not alerted by alerting module 114 as the new allele has an "unknown" meaning it has not been associated with a known disease. Platform 102 stores that new variant 415 and updates the variant classification for the patient. Platform 102 also stores that the new variant was queried against the patient's genomic sequencing results, changed classification, and that is unknown if the new variant is disease causing.

With continued reference to FIG. 4, variant comparing module 112 determines the patient has the new allele of "G" for new variant 410 and new variant 410 is likely disease causing based on data received from external resources 120. As the patient has the new allele and a change in patient's variant classification status, the clinician is notified by alerting module 114 of the change. Alerting module 114 alerts the clinician that the new allele is likely associated with a known disease. Platform 102 stores that new variant 405 and updates the variant classification for the patient. Platform 102 also stores that the new variant has been queried against the patient's genomic sequencing results, the changed classification, and that the new variant is likely disease causing.

Alerting module 114 sends an alert to the clinician, practice and/or clinical geneticist if the variant comparing module 112 determines there is a difference in a patient's variant classification status. The clinician, practice and/or clinical geneticist may contact the patient with a change in variant classification status and schedule an appointment for the patient using scheduling module 116. In one embodiment, scheduling module 116 automatically schedules an appointment for a patient when there is a change in variant classification status.

The bid price that triggers the initiation module 108 can be optimized such that a return on investment is optimized based on the anticipated number of variant classification changes in a patient population and number of scheduled appointments and associated revenue. Over time, this bid price can be an algorithm calculating the financial return from the anticipated number of variant status changes and bid price paid for cloud computing. As new rare diseases are identified at an increasing rate, the bid price can be continually increased to run the lookup more frequently if the provider organization has sufficient clinical geneticists available for patient appointments. As often there are more patients than available appointments for some providers, the bid price for computing power could be based on the anticipated frequency of which variants have a change in classification to likely disease causing.

Alerting module 114 notifies a clinician that a variant from the patient's genomic sequencing results has been reclassified and that a patient could be scheduled for an appointment to review the variant and likely disease diagnosis and any treatments.

Figure 2:
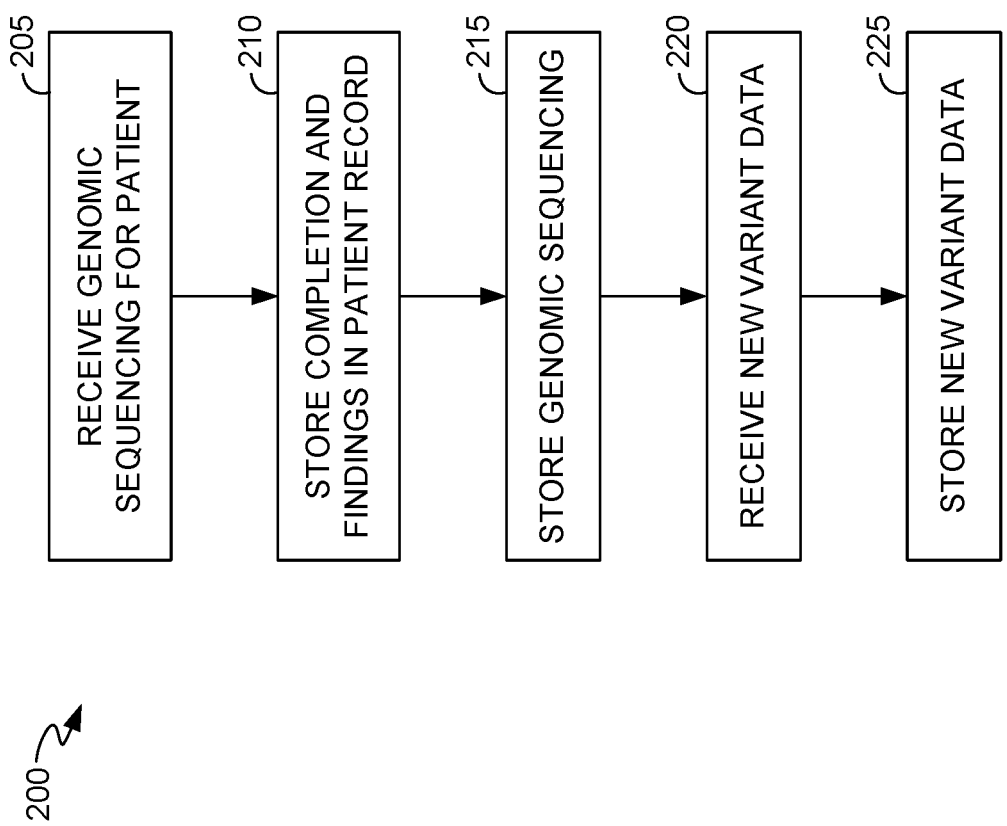
FIG. 2 depicts a flow chart for storing genomic sequencing and variant data in accordance with aspects of the invention.

FIG. 2 illustrates a method useful in a computing platform 102, in accordance with one or more implementations. With reference to FIG. 2, operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not necessarily limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

FIG. 2 illustrates method 200, in accordance with one or more implementations. Method 200 may be performed by one or more hardware processors configured by machine-readable instructions, utilizing electronic storage 122, and cold storage 126, to be utilized by modules 108, 110, 112, 114, and 116 in accordance with one or more implementations.

Operation 205 receives genomic sequencing data for a patient. Operation 210 stores in the patient's electronic medical record that the patient has genomic sequencing results and a pointer to the genomic sequencing results that are stored in cold storage 126 by Operation 215. The genomic sequence results data (e.g., variant information, base pair sequencing) can be quite large and that information is stored in cold storage 126 for utilization by platform 102 as needed or specified bid spot pricing is met.

Operation 220 receives new genomic variant data from external resources 120, such as genomic databases public and private. Operation 225 stores the new variant data in electronic storage 122 for variant comparing module 112 to compare to genomic sequencing results for one or more patients. Operations 220 and 225 may be performed on an on-going basis and stored in electronic storage 122 for when initiation module 108 initiates access of genomic sequencing results for one or more patients from cold storage 126. In another embodiment, Operations 220 and 225 are performed simultaneously or after initiation module 108 has initiated access of genomic sequencing results for one or more patients form cold storage 126.

Figure 3:
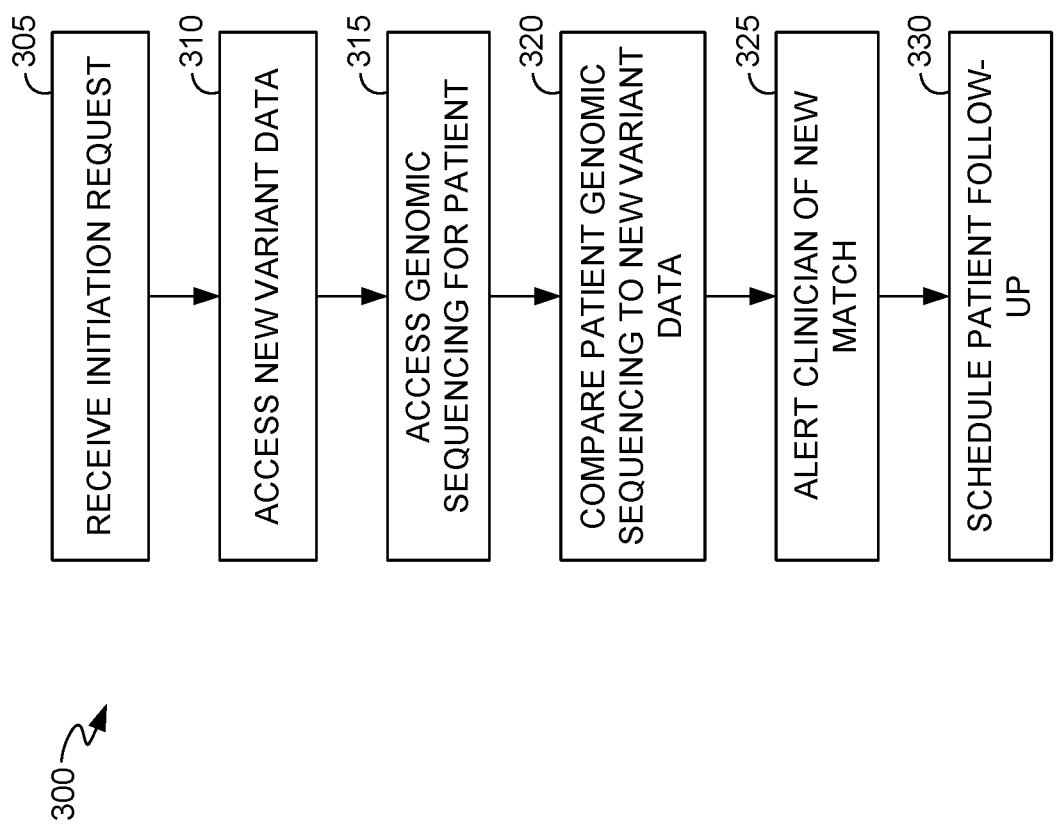
FIG. 3 depicts a flow chart for notifying a clinician of new potential variants for a patient in accordance with aspects of the invention.

FIG. 3 illustrates a method useful in a computing platform 102, in accordance with one or more implementations. With reference to FIG. 3, operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below is not necessarily limiting.

In some implementations, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

FIG. 3 illustrates method 300, in accordance with one or more implementations. Method 300 may be performed by one or more hardware processors configured by machine-readable instructions, utilizing electronic storage 122 and cold storage 126, to be utilized by modules 108, 110, 112, 114, and 116 in accordance with one or more implementations.

Operation 305 receives an initiation request to access genomic sequencing results for one or more patients from cold storage 126 and new variants from external resources 120. Operation 310 accesses new variant information from external resources 120 in real-time or, alternatively, accesses new variant information from electronic storage 122. Operation 315 accesses genomic sequencing results for one or more patients from cold storage 126. Operation 320 compares the genomic sequencing results for a patient to the new variant data from one or more external resources.

Operation 325 alerts, via graphical user interface, a clinician or practice group that a patient's genomic sequencing results match a new variant and the likely disease if the new variant is associated with a disease. Operation 330 schedules a follow-up appointment for the patient with the clinician or practice group so the clinician can discuss the new variant and likely disease with the patient along with any treatment options.

Although the present technology has been described in detail for the purpose of illustration based on what is currently considered to be the most practical and preferred implementations, it is to be understood such detail is solely for that purpose and the technology is not limited to the disclosed implementations, but, on the contrary, is intended to cover modifications and equivalent arrangements that are within the spirit and scope of the appended claims. For example, it is to be understood the present technology contemplates that, to the extent possible, one or more features of any implementation can be combined with one or more features of any other implementation.

The invention claimed is:

1. A method useful in a cloud environment for determining a patient has a newly discovered genomic variant, the method comprising:
   receiving genomic sequencing results for a patient;
   storing the genomic sequencing results for the patient in a cloud database, wherein genomic sequencing results include one or more gene variants that include an associated classification status;
   receiving an initiation request to access the genomic sequencing results for the patient from the cloud database;
   accessing and retrieving, via a network communication to a remote computing system, new genomic variants from a third party database, wherein one or more of the new genomic variants includes a classification status;
   performing a variant comparison to compare the genomic sequencing results for the patient to the new genomic variants to determine whether a match is found with one or more of the new genomic variants;
   identifying a change in classification status when the classification status of a matching new genomic variant is different from the associated classification status in the genomic sequencing results of the patient; and
   generating an alert that identifies the change in classification status and transmitting the alert to a remote device for access by a clinician.

2. The method of claim 1, further comprising:
   automatically, using the processor, scheduling a follow-up appointment with the clinician for the patient.

3. The method of claim 1, further comprising:
   receiving an electronic medical order from a clinician for the patient for genomic sequencing.

4. The method of claim 3, further comprising:
   receiving the genomic sequencing results for the patient in response to the electronic medical order.

5. The method of claim 1, wherein performing the variant comparison further comprising:
   extracting variants from the genomic sequencing results for the patient; and
   comparing the variants to the new genomic variants to determine if any variants match.

6. The method of claim 5, wherein the genomic sequencing results for the patient are compared to known genomic variants.

7. The method of claim 6, further comprising:
   receiving input from the clinician that the patient is undiagnosed based on the genomic sequencing results.

8. The method of claim 1, wherein the genomic sequencing results for the patient are stored in inactive cloud storage.

9. The method of claim 8, wherein the initiation request to access the genomic sequencing results from inactive cloud storage is sent when pricing for computing power is below a pre-set threshold.

10. A system configured determining a patient has a newly discovered genomic variant, the system comprising:
    one or more hardware processors configured by machine-readable instructions that when executed cause the processors to:
    receive genomic sequencing results for a patient;
    store the genomic sequencing results for the patient in a cloud database;
    receive an initiation request to access the genomic sequencing results for the patient from the cloud database;

access and retrieve, via a network communication to a remote computing system, new genomic variants from a third-party database;

perform a variant comparison to compare the genomic sequencing results for the patient to the new genomic variants to determine whether a match is found with one or more of the new genomic variants; and generate an alert that identifies the matching one or more new genomic variants and transmitting the alert to a remote device for access by a clinician.

11. The system of claim 10, further configured to:
automatically schedule a follow-up appointment with the clinician for the patient.

12. The system of claim 10, further configured to:
receive an electronic medical order from the clinician for the patient for genomic sequencing;
receive the genomic sequencing results for the patient in response to the electronic medical order; and
access known genomic variants from one or more third party database(s).

13. The system of claim 10, wherein the machine-readable instructions for performing the variant comparison further comprise instructions for causing the one or more processors to:
extract variants from the genomic sequencing results for the patient; and
compare the variants to the new genomic variants to determine if any variants match.

14. The system of claim 10, wherein the genomic sequencing results for the patient are stored in inactive cloud storage.

15. The system of claim 14, wherein the initiation request to access the genomic sequencing results from inactive cloud storage is sent when pricing for computing power is below a pre-set threshold.

16. A non-transitory computer-readable storage medium having instructions embodied thereon, the instructions being executable by one or more processors and when executed cause the one or more processors to at least perform actions comprising:
receiving genomic sequencing results for a patient;
storing the genomic sequencing results for the patient in a cloud database;
receiving an initiation request to access the genomic sequencing results for the patient from the cloud database;
accessing and retrieving, via a network communication to a remote computing system, new genomic variants from a third party remote database;
performing a variant comparison by comparing the genomic sequencing results for the patient to the new genomic variants to determine whether a match is found with one or more of the new genomic variants; and
generating an alert that identifies the matching one or more new genomic variants and transmitting the alert to a remote device for access by a clinician.

17. The storage medium of claim 16, further comprising executable instructions for:
automatically scheduling a follow-up appointment with the clinician for the patient.

18. The storage medium of claim 16, further comprising executable instructions for:
receiving an electronic medical order from the clinician for the patient for genomic sequencing;
receiving the genomic sequencing results for the patient m response to the electronic medical order, wherein the genomic sequencing results for the patient is compared to known genomic variants;
accessing known genomic variants from one or more third party database(s); and
receiving input from the clinician that the patient is undiagnosed based on the genomic sequencing results.

19. The storage medium of claim 18, wherein the instructions for performing the variant comparison further comprise instructions for causing the one or more processors to:
identify a change in classification status when the classification status of a matching new genomic variant is different from the associated classification status in the genomic sequencing results of the patient; and
generate an alert that identifies the change in classification status and transmit the alert to a remote device for access by one or more clinicians.

20. The storage medium of claim 16, wherein the initiation request to access the genomic sequencing results from the cloud database is initiated when pricing for computing power associated with the cloud database is below a pre-set threshold.

* * * * *